United States Patent [19]

Kende et al.

[11] 4,259,476

[45] Mar. 31, 1981

[54] NOVEL HETEROCYCLIC ANTHRACYCLINE COMPOUNDS

[76] Inventors: Andrew S. Kende, 19 Larchwood Dr., Pittsford, N.Y. 14534; Howard Newman, 11 Kuperman La., Monsey, N.Y. 10952

[21] Appl. No.: 26,392

[22] Filed: Apr. 2, 1979

[51] Int. Cl.³ .................... C07H 17/00; C07H 17/02; C07H 17/04

[52] U.S. Cl. ............................ 536/17 A; 260/346.71; 544/234; 544/235; 544/345; 544/349; 544/387; 548/125; 548/126; 548/127; 548/255; 548/257; 549/42

[58] Field of Search ...................................... 536/17 A

[56] References Cited

U.S. PATENT DOCUMENTS

| | | | |
|---|---|---|---|
| 4,020,270 | 4/1977 | Arcamone et al. | 536/17 A |
| 4,039,663 | 8/1977 | Arcamone et al. | 536/17 A |
| 4,067,969 | 1/1978 | Penco et al. | 536/17 A |
| 4,077,988 | 3/1978 | Arcamone et al. | 536/17 A |

*Primary Examiner*—Johnnie R. Brown
*Attorney, Agent, or Firm*—Edward A. Conroy, Jr.

[57] ABSTRACT

Novel heterocyclic anthracycline compounds having antitumor activity against murine P388 leukemia in mice.

8 Claims, No Drawings

NOVEL HETEROCYCLIC ANTHRACYCLINE COMPOUNDS

DESCRIPTION OF THE INVENTION

This invention is concerned with new compounds of the formula (I):

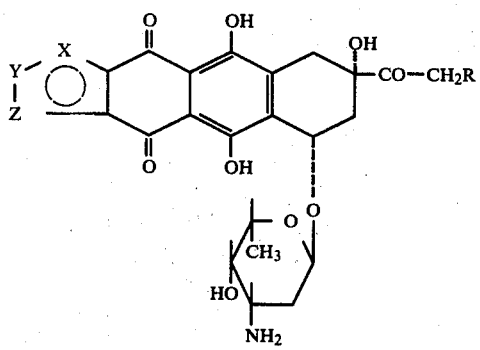

wherein R is hydrogen or hydroxy and X, Y or Z may be sulfur with the proviso that when X is sulfur then Y and Z are both CH and when Y is sulfur then X and Z are both CH and when Z is sulfur then X and Y are both CH.

This invention is also concerned with new compounds of the formula (II):

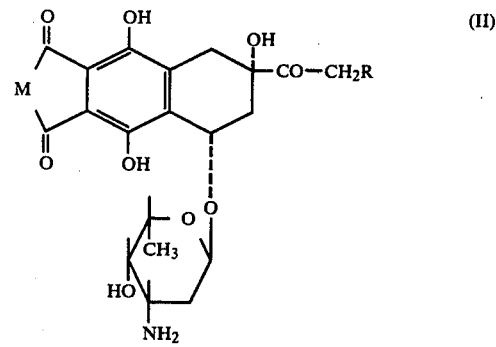

wherein R is hydrogen and hydroxy and M may be a heterocyclic ring such as

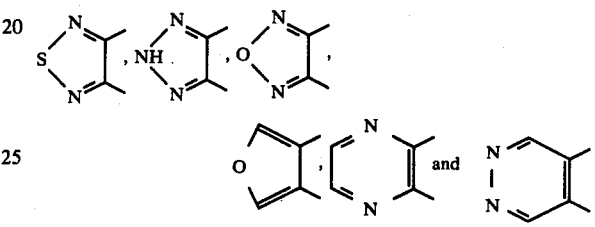

The compounds of formula (I) may be prepared according to the following reaction scheme:

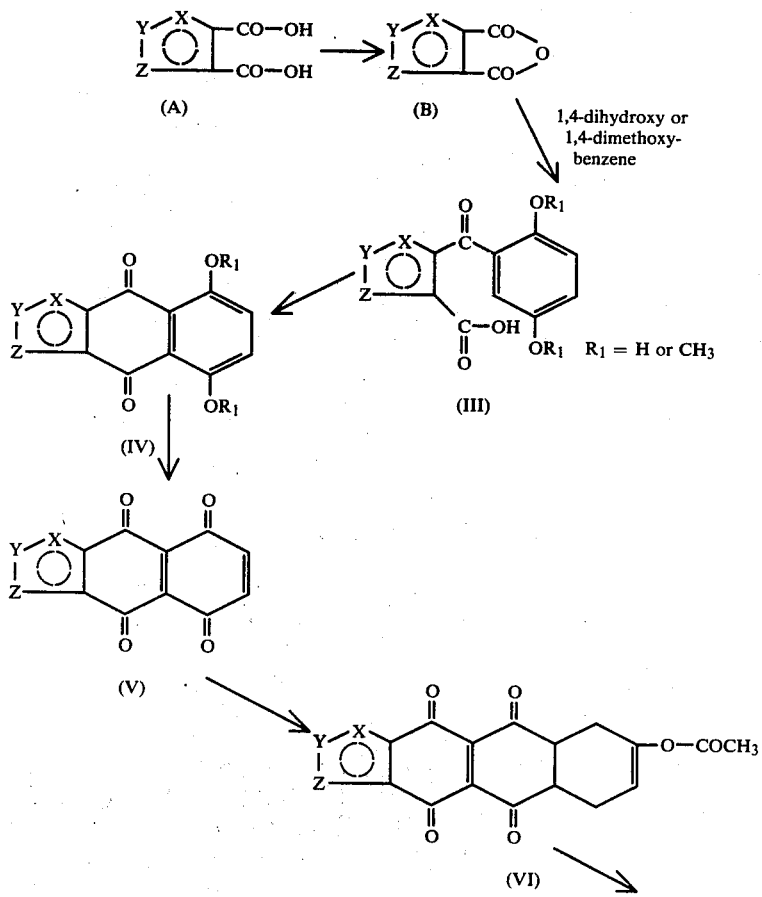

-continued
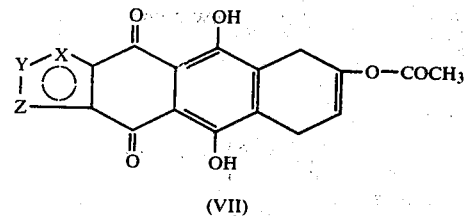
(VII)
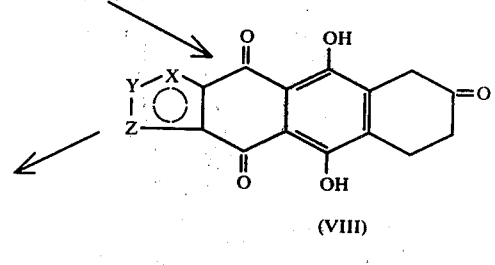
(VIII)
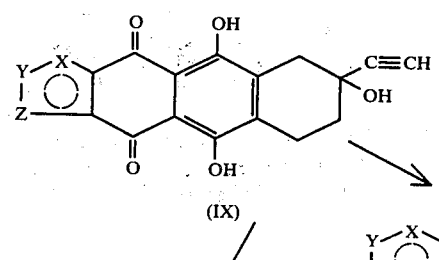
(IX)
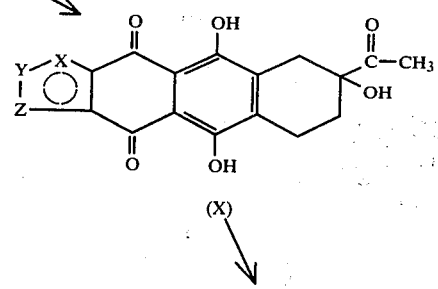
(X)
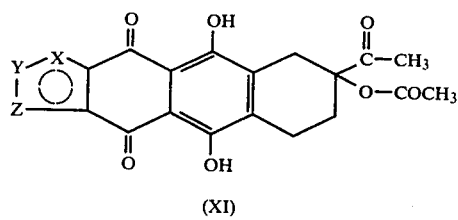
(XI)
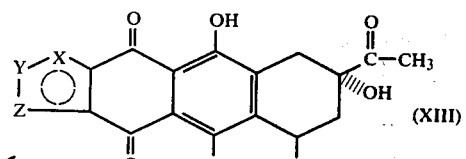
(XIII)
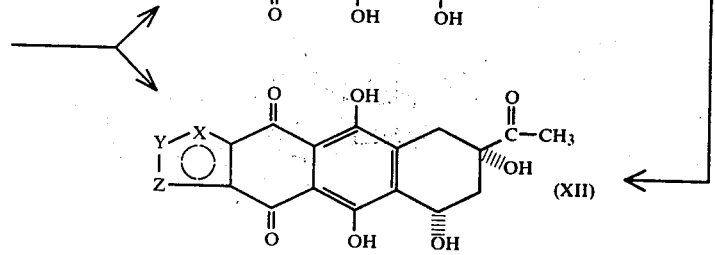
(XII)

-continued
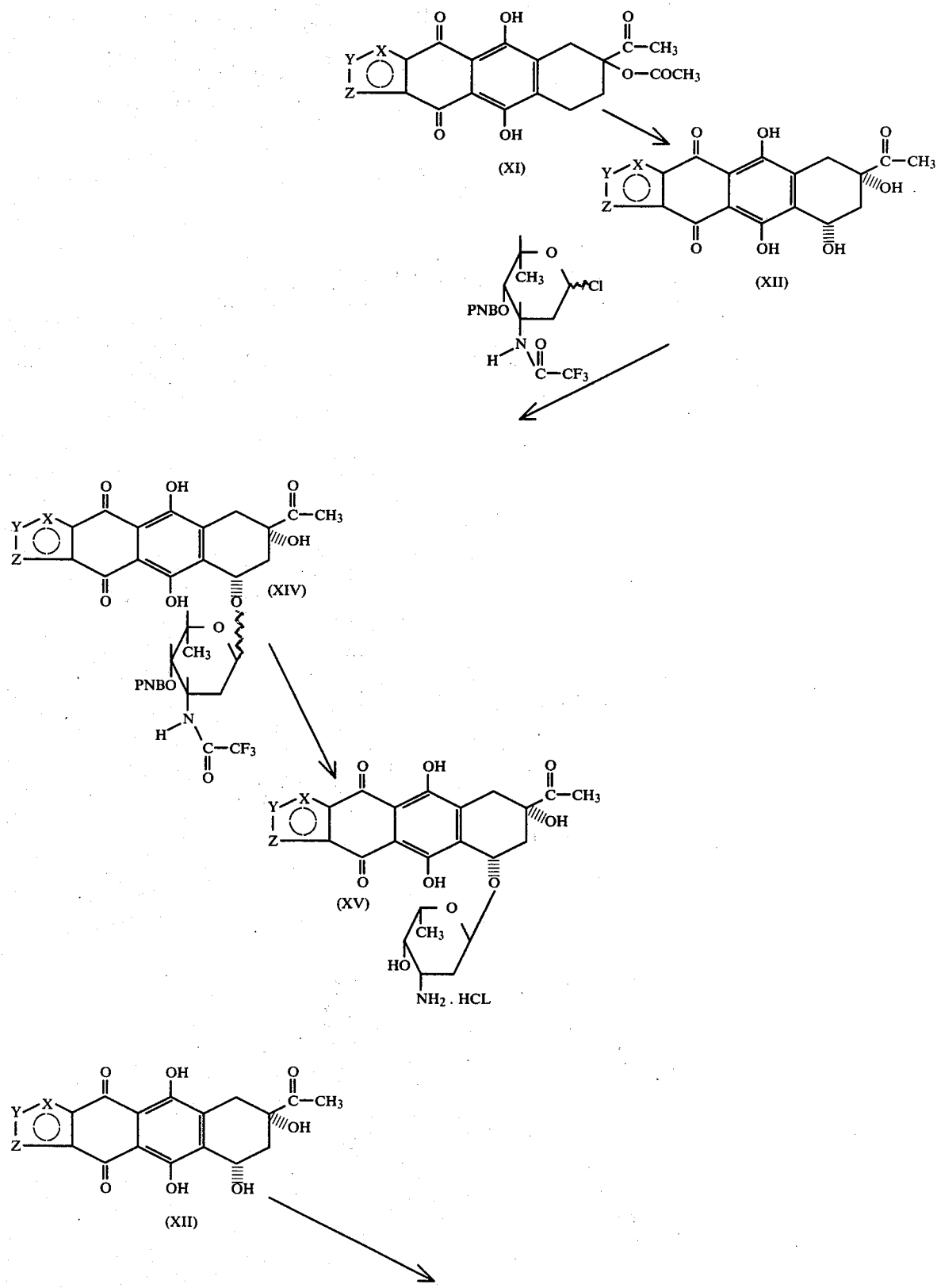

-continued
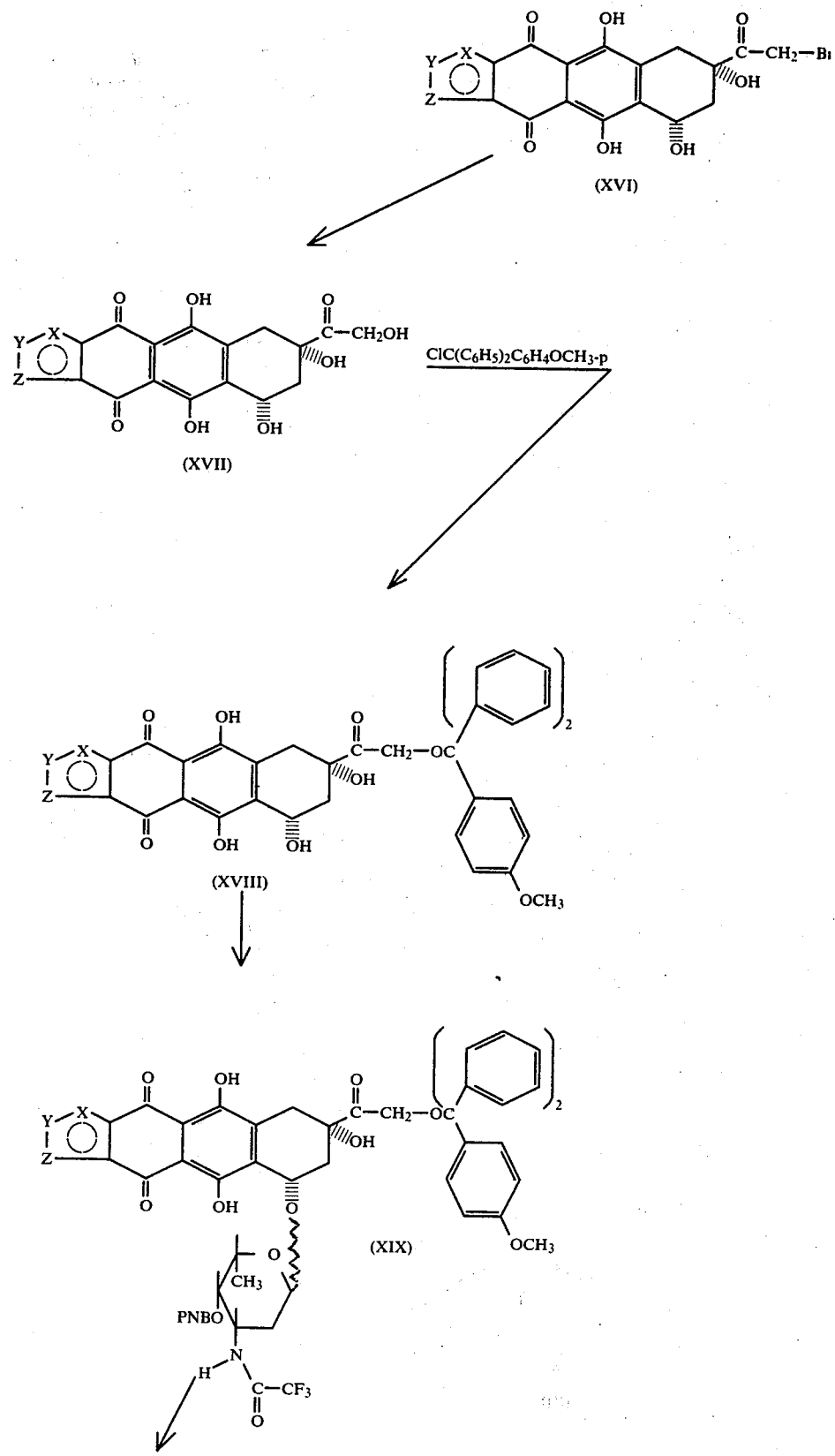

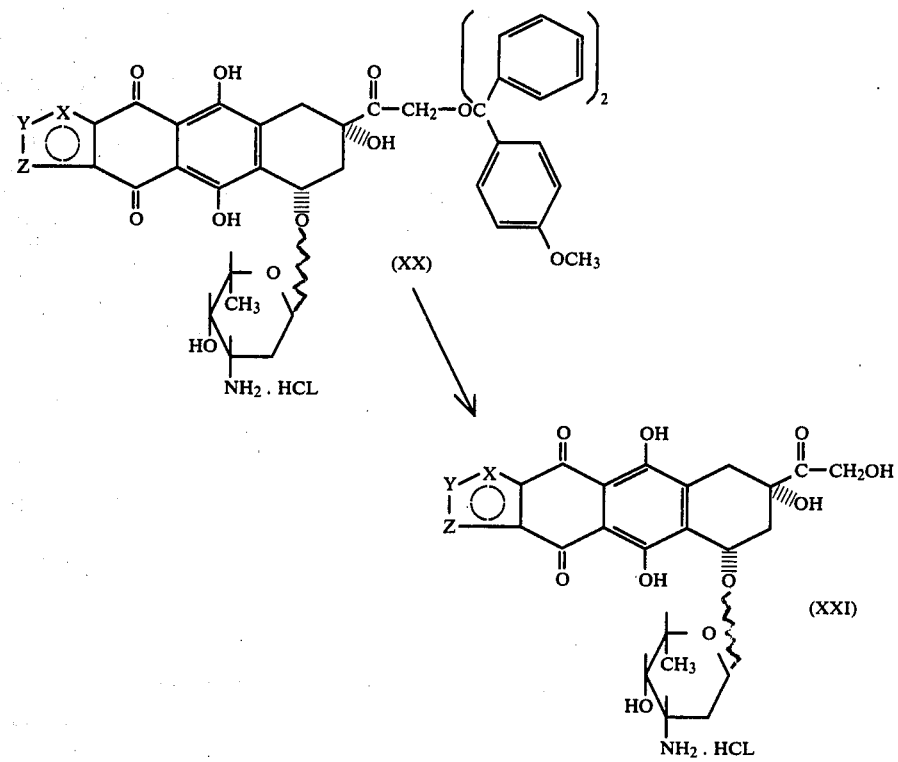

wherein X, Y and Z are as previously described.

The appropriate thiophenedicarboxylic acid (A) is converted to the corresponding thiophenedicarboxylic acid anhydride (B) by suspending in chloroacetyl chloride, acetic anhydride or preferably trifluoroacetic anhydride and heating at reflux while removing excess solvent.

The anhydride in cold methylene chloride is treated with aluminum chloride and p-dimethoxybenzene for 16–24 hours to provide the corresponding dimethoxybenzoylthiophene carboxylic acid (III) which is, in turn, treated with sulfuric acid to produce the dihydroxynaphthothiophenedione, dimethyl ether (IV). Treatment of the latter compound with either silver (II) oxide or lead tetraacetate gives naphthothiophenetetrone (V). Condensation of (V) with 2-acetoxybutadiene in glacial acetic acid for 20–60 hours gives acetoxytetrahydroanthrathiophenetetrone (VI) which upon treatment with sodium acetate in acetic acid at 110°–130° C. isomerizes to acetoxydihydrodihydroxyanthrathiophenedione (VII). Compound (VI) or compound (VII) is suspended in a solvent such as p-dioxane or ethanol and treated with 6 N hydrochloric acid under reflux conditions for 20 min. to 6 hrs. to provide trione (VIII). Trione (VIII) in dry tetrahydrofuran is then treated with ethynylmagnesium bromide and acetylene at room temperature under $N_2$ for 16 hours and purified by column chromatography on Florisil ® to obtain dihydroethynyltrihydroxyanthrathiophenedione (IX).

In proceeding with the synthesis, compound (IX) can be treated in two different ways. The ethynyl compound in methanol:water (7:2) is treated with mercury resin [prepared by the method of Newman, J.A.C.S., 75, 4740 (1953)] heated under reflux for 16 hours to give acetyldihydrotrihydroxyanthrathiophenedione (X) or alternatively compound (IX) can be suspended in acetic acid and treated with mercuric acetate, mercury resin or mercuric oxide in aqueous sulfuric acid for 16 hrs. to give acetoxyacetyldihydrodihydroxyanthrathiophenedione (XI).

Either of the above compounds (X) or (XI) in carbon tetrachloride is treated with bromine and azo-bis-isobutyronitrile and heated to 100° C. for 0.5 to 3 hours and then with potassium carbonate in tetrahydrofuran and water for several hours and finally with oxalic acid to obtain a mixture of cis and trans-dihydrotetrahydroxyacetylanthrathiophenediones (XII) and (XIII). Either the purified trans-diol (XIII) or the crude mixture of cis and trans-diol upon treatment with trifluoroacetic acid is converted to pure cis-dihydrotetrahydroxyacetylanthrathiophenedione (XII).

Compound (XII), dissolved in chloroform, is treated with mercuric cyanide, mercuric bromide and 3 A molecular sieves, then with 4-O-p-nitrobenzoyl-3-N-trifluoroacetyldaunosaminyl chloride over a 24 hour period to obtain a mixture of the α and β-anomers of the blocked glycoside (XIV). This mixture can be separated by thin-layer chromatography to give the pure α and β-anomers.

The blocked glycoside (XIV) in tetrahydrofuran is deblocked by treatment with 0.1 N sodium hydroxide solution at 0°–5° C. for about 4 hours and then treated with hydrogen chloride to obtain the hydrochloride of daunomycin analog (XV), an acetyl-(3-amino-2,3,6-trideoxy-lyxo-hexopyranosyloxy)tetrahydrotrihydroxyanthrathiophenedione hydrochloride.

Alternatively, compound (XII), in chloroform, is treated with bromine to give bromoacetyldihydrotetrahydroxyanthrathiophenedione (XVI). Compound (XVI) is then suspended in 80% aqueous acetone and treated with 0.1 N sodium hydroxide to give dihydrohydroxyacetyltetrahydroxyanthrathiophenedione (XVII).

Compound (XVII) in pyridine is treated with anisylchlorodiphenylmethane at 0° C. for four days to obtain, after chromatography, anisyldiphenylmethyl ether (XVIII). The latter compound, in tetrahydrofuran, is then treated with mercuric bromide, mercuric cyanide and 3 A molecular sieves, then with 4-O-p-nitrobenzoyl-3-N-trifluoroacetyldaunosaminyl chloride in dichloromethane to obtain blocked glycoside (XIX).

Blocked glycoside (XIX) is then treated with dilute sodium hydroxide and then with acetic acid to obtain ether (XX) and finally with HCl to obtain the heterocyclic analog (XXI) of adriamycin.

The heterocyclic compounds of Formula (II) may be prepared by the same methods previously described for the thiophene analog.

The compounds of the present invention are active anti-cancer agents as established in the following test.

LYMPHOCYTIC LEUKEMIA P388 TEST

Reference: Cancer Chemotherapy Reports 3, No. 2, page 9 (1972).

The animals used are $BDF_1$ or $CDF_1$ mice all of one sex, weighing a minimum of 17 g. and all within a 3 g. weight range. There are 6 animals per test group and 10 mice in placebo control groups. The tumor transplant is administered by intraperitoneal injection of 0.1 ml. of dilute ascitic fluid containing $10^6$ cells of lymphocytic leukemia P388. The test compounds are dissolved in saline and are administered intraperitoneally on day plus one, (relative to tumor inoculation) at various doses. The animals were weighed and survivors are recorded on a regular basis for 30 days. The median survival time and the ratio of survival time for treated (T)/control (C) animals are calculated. The positive control compound is 5-fluorouracil.

The results of this test on representative compounds of the present invention appear in Table I. The criterion for efficacy is $T/C \times 100 \geq 125\%$.

Chem., 19, 1671 (1954)]} is suspended in 50 ml. of chloroacetyl chloride and is heated at reflux for 5.5 hours. Excess chloroacetyl chloride is distilled under reduced pressure. The residue is poured into 100 ml. of water and the resulting crystals are collected to yield 16.1 g. of 3,4-thiophenedicarboxylic anhydride.

A 13.0 g. portion of the preceding product is suspended in 300 ml. of methylene chloride and is cooled to 0° C. A 25.0 g. portion of aluminum chloride is added and the mixture is stirred for 0.5 hours at 0° C., then at room temperature for 0.75 hours. The mixture is cooled to 0° C. and 24.0 g. of p-dimethoxybenzene in 50 ml. of methylene chloride is added dropwise. The reaction mixture is allowed to warm to room temperature and is stirred for 16 hours. The solution is poured into ice/concentrated hydrochloric acid and the resulting mixture is extracted with three 300 ml. portions of ethyl acetate. The combined organic extracts are extracted with three 300 ml. portions of saturated sodium bicarbonate. The basic extracts are combined and washed with 100 ml. of ethyl acetate. The aqueous solution is acidified with concentrated hydrochloric acid and is extracted with three 150 ml. portions of ethyl acetate. The combined organic extracts are washed once with saturated sodium chloride, dried over sodium sulfate and evaporated in vacuo to yield 16.9 g. of 3-(2,5-dimethoxybenzoyl)-4-thiophene carboxylic acid; m.p. 108°–110° C.

A 2.6 g. portion of the above product is dissolved in 60 ml. of concentrated sulfuric acid and is heated on a steam bath with occasional stirring for 20 minutes. The solution is poured onto crushed ice. The resulting solution is extracted with several portions of chloroform. The combined chloroform extracts are washed with two 100 ml. portions of 2% aqueous sodium hydroxide, then with 50 ml. of water. The organic solvent is dried over sodium sulfate and evaporated in vacuo to yield 1.61 g. of 5,8-dihydroxynaphtho[2,3-c]thiophene-4,9-dione, dimethyl ether; m.p. 181°–182° C.

A 550 mg. portion of the preceding compound is

TABLE I

| Lymphocytic Leukemia P388 Test | | | |
|---|---|---|---|
| Compound | Dose (mg./kg.) | Median Survival (Days) | T/C × 100 (Percent) |
| 8α-Acetyl-6β-[(3-amino-2,3,6-trideoxy-α-L-lyxo-hexopyranosyl)-oxy]-6,7,8,9-tetrahydro-5,8β,10-trihydroxyanthra[2,3-c]thiophene-4,11-dione, hydrochloride | 2.5 | 20.0 | 174 |
|  | 1.2 | 17.5 | 152 |
|  | 0.6 | 17.0 | 148 |
|  | 0.3 | 16.0 | 139 |
| Control | 0 | 11.5 |  |
| 5-Fluorouracil | 200 | 14.5 | 126 |
| 7β(and/or 8α)-Acetyl-9α(and/or 6β)[(3-amino-2,3,6-trideoxy-α-L-lyxo-hexopyranosyl)oxy-6,7,8,9-tetrahydro-5,7α,10 (and/or 5,8α,10)-trihydroxyanthra[2,3-b]thiophene-4,11-dione, hydrochloride | 2.5 | 15.0 | 136 |
|  | 1.2 | 16.0 | 146 |
|  | 0.6 | 16.0 | 146 |
|  | 0.3 | 14.5 | 132 |
| Control | 0 | 11.0 |  |
| 5-Fluorouracil | 200 | 19.0 | 173 |
| 7β(and/or 8α)-Acetyl-9α(and/or 6β)-[(3-amino-2,3,6-trideoxy-β-L-lyxo-hexopyranosyl)oxy]-6,7,8,9-tetrahydro-5,7α,10 (and/or 5,8β,10-trihydroxyanthra[2,3-b]thiophene-4,11-dione, hydrochloride | 10.0 | 15.5 | 141 |
|  | 5.0 | 14.0 | 127 |
|  | 2.5 | 14.0 | 127 |
| Control | 0 | 11.0 |  |
| 5-Fluorouracil | 200 | 19.0 | 173 |

EXAMPLE 1

8α-Acetyl-6β-[(3-amino-2,3,6-trideoxy-α-L-lyxo-hexopyranosyl)oxy]-6,7,8,9-tetrahydro-5,8β,10-trihydroxyanthra[2,3-c]thiophene-4,11-dione, hydrochloride A 25.5 g. portion of 3,4-thiophenedicarboxylic acid {prepared by the method of Kornfeld and Jones [J. Org.

suspended in 20 ml. of acetone and is heated to reflux. A 1.0 g. portion of silver (II) oxide is added and the mixture is sonicated briefly. The mixture is stirred and 4 ml. of 6 N nitric acid is added. Stirring is continued for 3 minutes, then the mixture is cooled in an ice bath and filtered to yield 250 mg. of naphtho[2,3-c]thiophene-4,5,8,9-tetraone.

A 992 mg. portion of naphtho[2,3-c]thiophene-4,5,8,9-tetraone (prepared as described above), 1.10 g. of 2-acetoxybutadiene and 4.0 ml. of glacial acetic acid is stirred for 48 hours at room temperature. The mixture is filtered and the filter cake is washed with ether and dried in vacuo to yield 1.287 g. of 7-acetoxy-5a,6,9,9a-tetrahydroanthra[2,3-c]thiophene-4,5,10,11-tetraone.

A 867 mg. portion of the preceding product is suspended in 10 ml. of glacial acetic acid and is heated to 110° C. The reaction mixture is placed under nitrogen and treated with 280 mg. of anhydrous sodium acetate. The mixture is stirred for 15 minutes, allowed to cool to room temperature and filtered. The filter cake is washed with ether, then dried in vacuo to yield 652 mg. of 7-acetoxy-6,9-dihydro-5,10-dihydroxyanthra[2,3-c]thiophene-4,11-dione.

A 849 mg. amount of the above compound (prepared in the manner described) is suspended in 33.0 ml. of p-dioxane and 14.0 ml. of 6 N hydrochloric acid. The mixture is placed under nitrogen and heated at 120° C. with stirring for 20 minutes. The reaction mixture is allowed to cool to room temperature, is diluted with water and filtered. The filter cake is washed with water, then ether and is dried in vacuo to yield 746 mg. of 6,9-dihydro-5,10-dihydroxyanthra[2,3-c]thiophene-4,7,11,8(H)trione.

The entire amount of the above compound (746 mg.) is dissolved in 800 ml. of dry tetrahydrofuran and is added dropwise to a solution of ethynylmagnesium bromide and acetylene. The reaction mixture is stirred at room temperature for 16 hours, then is quenched with 10% oxalic acid. The mixture is poured into water and extracted with several 40 ml. portions of chloroform. The combined organic extracts are washed with water, dried over sodium sulfate, and evaporated in vacuo. The residue is chromatographed on a short Florisil ® column, eluting with 3.0% methanol/methylene chloride. This product which is still a mixture is ethynylated a second time under the above reaction conditions to yield 591 mg. of 6,7,8,9-tetrahydro-7-ethynyl-5,7,10-trihydroxyanthra[2,3-c]thiophene-4,11-dione.

A 101 mg. amount of the preceding compound is suspended in a mixture of 70 ml. of methanol and 20 ml. of water and is treated with 1.5 g. of Hg-resin [prepared by the method of Newman, *J. Amer. Chem. Soc.*, 75, 4740 (1953), using Amberlite ® CG-120 in place of Dowex ®-50]. The reaction mixture is heated at reflux overnight. The hot mixture is filtered and the filter cake is washed with chloroform. The filtrate is poured into water and extracted with chloroform. The combined extracts are washed with water, dried over sodium sulfate, and evaporated. The residue is dissolved in methylene chloride and eluted through a 1"×1" Florisil ® column with methylene chloride, gradually increasing the polarity to 3% methanol/methylene chloride. The eluate is evaporated to yield 81.0 mg. of 7-acetyl-6,7,8,9-tetrahydro-5,7,10-trihydroxyanthra[2,3-c]thiophene-4,11-dione; m.p. 189°–191° C. (dec.).

Alternatively, 195 mg. of 6,9-dihydro-7-ethynyl-5,7,10-trihydroxyanthra[2,3-c]thiophene-4,11,8(H)-dione is suspended in 75 ml. of ethyl acetate and is treated with 400 mg. of mercuric acetate. The mixture is stirred overnight at room temperature, then hydrogen sulfide gas is bubbled through the suspension for several minutes. The mixture is filtered through diatomaceous earth and the filter cake is washed with chloroform until the filtrate from the filter cake is colorless. The filtrate is evaporated in vacuo to yield a crude product which is chromatographed through a 1"×1" Florisil ® column and eluted with 3% methanol/methylene chloride to yield 177 mg. of 7-acetoxy-7-acetyl-6,7,8,9-tetrahydro-5,10-dihydroxyanthra[2,3-c]thiophene-4,11-dione.

A 52.0 mg. portion of 7-acetyl-6,7,8,9-tetrahydro-5,7,10-trihydroxyanthra[2,3-c]thiophene-4,11-dione is dissolved in 100 ml. of carbon tetrachloride and treated with 17.0 mg. of azoisobutyronitrile and 0.17 M. bromine in 1.3 ml. of carbon tetrachloride. The reaction mixture is heated at reflux for 1.5 hours then is treated with an additional 10.0 mg. of azoisobutyronitrile. After a total of 3 hours, the mixture is cooled to room temperature and stirred with a solution of 420 mg. of potassium carbonate in 60 ml. of 50% aqueous tetrahydrofuran for several minutes. The mixture is poured into water, acidified with 5% oxalic acid, and extracted with chloroform. The combined organic extracts are dried over sodium sulfate concentrated and chromatographed on three preparative silica gel thin layer plates. The three most polar bands from each plate are separated and eluted with 3% methanol/methylene chloride. The combined least polar band eluates yield 25 mg. of the above starting material. The second most polar band eluates yield a total of 3 mg. of cis-(±)-8-acetyl-6,7,8,9-tetrahydro-5,6,8,10-tetrahydroxyanthra[2,3-c]thiophene-4,11-dione and the combined most polar band eluates yield a total of 10 mg. of trans-(±)-diol.

The above trans-material (10 mg.) is dissolved in 5.0 ml. of trifluoroacetic acid and is allowed to stand at room temperature for four hours. The mixture is poured into water and extracted with chloroform. The extracts are combined, dried over sodium sulfate and evaporated. The residue is dissolved in 25 ml. of methanol and is heated at reflux for 2 hours. The resulting solution is poured into water, extracted with chloroform, dried over sodium sulfate and concentrated. Chromatography over silica gel and elution with 3% methanol/methylene chloride yields 8 mg. of cis-(±)-8-acetyl-6,7,8,9-tetrahydro-5,6,8,10-tetrahydroxyanthra[2,3-c]thiophene-4,11-dione.

A 140 mg. portion of 7-acetoxy-7-acetyl-6,7,8,9-tetrahydro-5,10-dihydroxyanthra[2,3-c]thiophene-4,11-dione is dissolved in 150 ml. of carbon tetrachloride and is treated with 0.17 M. bromine in 3.1 ml. of carbon tetrachloride, and 20.0 mg. of azoisobutyronitrile. The reaction mixture is heated at reflux for 20 minutes, then is treated with additional portions of azoisobutyronitrile and bromine solution. After a total of 40 minutes, 700 mg. of potassium carbonate in 50% aqueous tetrahydrofuran is added and the mixture is stirred at room temperature for 5 minutes. The reaction mixture is poured into water, extracted with chloroform, dried over sodium sulfate and evaporated. The residue is dissolved in 10 ml. of trifluoroacetic acid and is stirred at room temperature for 2 hours. This mixture is poured into water and extracted with chloroform. The solvent is removed in vacuo and the residue is suspended in methanol. Saturated potassium carbonate is added and the reaction mixture is stirred under nitrogen for 4 hours. The mixture is acidified with 5% oxalic acid and extracted with chloroform. The extracts are dried over sodium sulfate and concentrated. The residue is chromatographed over silica gel as previously described to yield 12 mg. of cis-(±)-8-acetyl-6,7,8,9-tetrahydro-5,6,8,10-tetrahydroxyanthra[2,3-c]thiophene-4,11-dione.

A 15.0 mg. amount of the above product (prepared in the manner described) is dissolved in 2.0 ml. of dry chloroform and stirred with 21.0 mg. of mercuric cyanide, 15.0 mg. of mercuric bromide and 60.0 mg. of powdered 3A molecular sieves for one hour, then 4-O-p-nitrobenzoyl-3-N-trifluoroacetyldaunosaminyl chloride prepared from 21.0 mg. of di-p-nitrobenzoyl sugar is added. The reactin mixture is stirred overnight and treated with additional portions, as above, of mercuric cyanide, mercuric bromide, molecular sieves, and chlorosugar. Six hours after the second portion of sugar is added, the mixture is filtered. The filter cake is washed with chloroform, and the filtrate is washed with two 20 ml. portions of 30% aqueous potassium iodide and 10 ml. of water. The organic solvent is dried over sodium sulfate and concentrated. The residue is chromatographed over silica gel to yield 11.0 mg. of α-anomer, 8β-acetyl-6,7,8,9-tetrahydro-5,8β,10-trihydroxy-6β-{[2,3,6-trideoxy-4-o-(4-nitrobenzoyl)-3-[(trifluoroacetyl)amino]-$\underline{L}$-lyxo-hexopyranosyl]oxy}-anthra[2,3-c]-thiophene-4,11-dione and 8.0 mg. of β-anomer.

A 31.0 mg. amount of the above α-anomer (prepared in the manner described) is dissolved in 9 ml. of tetrahydrofuran and cooled to 0° C. The solution is degassed 3 times, treated with 5 ml. of 0.1 $\underline{N}$ sodium hydroxide, degassed 3 more times and placed under nitrogen. After 4.5 hours at 0° C., the mixture is acidified with dilute hydrochloric acid, poured into 20 ml. of water and extracted with chloroform. The chloroform is discarded and the aqueous phase is made basic to pH 8.0 with 0.1 $\underline{N}$ sodium hydroxide, then is extracted with chloroform until no more colored material is extracted (note: the pH of the aqueous phase is maintained at 8.0 during these extractions.) The basic extracts are washed with saturated sodium bicarbonate, dried over sodium sulfate, and evaporated to yield 17 mg. of free base.

The free base is dissolved in 1.0 ml. of methanol and is treated with 1.0 ml. of 0.18 M. ethanolic hydrogen chloride. The amine hydrochloride salt is precipitated with diethyl ether and the solvent is decanted. The residue is air dried, then is dried in vacuo to yield 14 mg. of 8α-acetyl-6β-[(3-amino-2,3,6-trideoxy-α-$\underline{L}$-lyxo-hexopyranosyl)oxy]-6,7,8,9-tetrahydro-5,8β,10-trihydroxyanthra[2,3-c]thiophene-4,11-dione hydrochloride.

EXAMPLE 2

7β(and/or 8α)-Acetyl-9α(and/or 6β)-[(3-amino-2,3,6-trideoxy-α-L(or-β-L)-lyxo-hexopyranosyl)oxy]-6,7,8,9-tetrahydro-5,7α,10(and/or 5,8β,10)-trihydroxyanthra[2,3-b]thiophene-4,11-dione, hydrochloride A 11.9 g. portion of 2,3-thiophenedicarboxylic acid {prepared by the method of Binder and Stanetty [Synthesis, 200–201, (March 1977)]} is suspended in 54.0 ml. of acetic anhydride then is stirred and heated under reflux at 190° C. for 30 minutes. The solution is cooled in a ice bath for a few minutes, then is poured onto ice with stirring. The mixture is allowed to stand one hour and the product is collected and air dried to yield 7.7 g. of thiophene-2,3-carboxylic acid anhydride.

To a stirred suspension of 7.7 g. of the above product and 7.4 g. of 1,4-dimethoxybenzene in 70 ml. of methylene chloride maintained at 15°–23° C. in a ice bath is added portionwise 13.9 g. of powdered anhydrous aluminum chloride. The reaction mixture is allowed to stir for 24 hours at room temperature under anhydrous conditions, then is poured into ice water. The mixture is made acidic with concentrated hydrochloric acid and is extracted 4 times with ethyl ether. The combined ether extracts are extracted once with 1 $\underline{N}$ aqueous sodium hydroxide. The alkaline extract is washed once with ether then is diluted with ice and made acid again with concentrated hydrochloric acid to provide an orange oil and a yellow flocculent precipitate. The oil solidified on standing with scratching and the yellow floculent material above is decanted from the orange solid with the water. The orange solid is collected, washed with water and air dried. The above decantation, filtration and washing process is repeated to obtain additional orange solid to yield a total of 8.1 g. of 3-(2,5-dimethoxybenzoyl)-2-thiophenecarboxylic acid.

A 73.0 g. amount of the preceding product (prepared as described above) is mixed with 830 ml. of concentrated sulfuric acid and is stirred and heated on a steam bath at 95° C. for 20 hours. The reaction mixture is allowed to cool to 70° C., then is poured into 3 liters of ice water with stirring. The resulting precipitate is collected by filtration through a pad of diatomaceous earth. The product-diatomaceous earth mixture is dried at 50° C. in a atmospheric steam oven, then is charged to a Soxhlet extractor and is continuously extracted for 22 hours with acetone. The acetone extract is concentrated almost to dryness in vacuo, then 1200 ml. of ethanol is added to the maroon solid and the mixture is heated to a boil. The mixture is chilled in a ice bath for ½ hour to precipitate a product. The product is collected, washed with ethanol and dried to yield 21.0 g. of 1,4-dihydroxynaphthoquinone thiophene.

A suspension of 3.2 g. of the above product in 120 ml. of glacial acetic acid contained in a 400 ml. beaker is treated with 18.0 g. of lead (IV) acetate added in one portion. The mixture is stirred at room temperature for 15 minutes, then is diluted with ice-water. After stirring for 4 minutes the mixture is filtered through a pad of diatomaceous earth and the product collected is washed with water. The product on the filter pad is dried overnight, in vacuo. The dark brown solid along with some diatomaceous earth from the filter pad that could not be separated is transferred to a Soxhlet extraction thimble and is continuously extracted with methylene chloride for 2 hours. The methylene chloride is evaporated in vacuo to yield 1.75 g. of crude product as a deep maroon solid. The product is purified by suspending and stirring with slow evaporation in methylene chloride to crystallize a total of 850 mg. of naphtha[2,3-b]thiophene-4,7,8,9-tetrone. A suspension of 0.80 g. of the above product, a catalytic amount of hydroquinone and 1.10 g. of 2-acetoxy-1,3-butadiene in 2.0 ml. of acetic acid is stirred at room temperature under nitrogen for two days. The yellow precipitate is collected, washed with 0.5 ml. of acetic acid, ether, and dried in vacuo to yield 0.658 g. of a regioisomeric mixture of 5a,6,9,9a-tetrahydro-7-and-8-hydroxyanthra[2,3-b]thiophene-4,5,10,11-tetraone-7-and-8-acetate.

To a suspension of 63 mg. of the above compound in 7.0 ml. of acetic acid is added one equivalent of anhydrous sodium acetate. The resulting mixture is heated at 130° C. under nitrogen for 5 minutes. The mixture is cooled to room temperature, then water is added to yield a red precipitate. The precipitate is collected, washed with water and dried in vacuo to give 56.7 mg. of a regioisomeric mixture of 6,9-dihydro-5,7,10-and 5,8,10-trihydroxyanthra[2,3-b]thiophene-4,11-dione-7-and-8-acetate.

A 0.53 g. amount of the preceding compound (prepared as described above) in 200 ml. of ethanol is degassed and flushed with nitrogen three times. To this suspension is added 20 ml. of 6 N hydrochloric acid. The resulting mixture is degassed, flushed once with nitrogen and heated to reflux under nitrogen for 6 hours. The mixture is cooled to room temperature and the precipitate is collected by filtration and washed with cold ethanol. The filtrate is diluted with water and extracted with chloroform. The chloroform extract is washed with water and dried over anhydrous sodium sulfate. The solvent is removed in vacuo to give a red solid which is combined with the previous precipitate and dried in vacuo to give 0.466 g. of a regioisomeric mixture of 6,7,8,9-tetrahydro-5,10-dihydroxyanthra[2,3-b]thiophene-4,7,11(8H)-and 4,8,11(7H)-trione.

Acetylene gas, purified by passing through a dry ice acetone trap, then through concentrated sulfuric acid is bubbled rapidly through 200 ml. of freshly distilled tetrahydrofuran, under nitrogen for one hour. Then 6.5 ml. of 2.94 molar ethyl-magnesium bromide in ether is added slowly. After the addition of ethylmagnesium bromide is complete the passage of acetylene gas is continued and 0.28 g. of the preceding product in dry tetrahydrofuran is added with stirring. The flow of acetylene is continued for one hour longer, then the reaction mixture is allowed to stir at room temperature under nitrogen overnight. After quenching with saturated oxalic acid, the solution is extracted with chloroform. The chloroform extract is washed copiously with water, dried over anhydrous sodium sulfate and evaporated to dryness. The residue in chloroform is chromatographed on 0.5 mm. silica gel preparative thin layer chromatographic plates, eluting with 3% methanol in methylene chloride to yield 0.172 g. of a regioisomeric mixture of (±)-6,7,8,9-tetrahydro-5,7,10-and 5,8,10-trihydroxy-7-and-8-ethynlanthra-[2,3-b]thiophene-4,11-dione.

To a stirred solution of 34.9 mg. of the above compound in 50 ml. of ethyl acetate is added 104.7 mg. of mercuric acetate. The resulting mixture is stirred at room temperature overnight, then hydrogen sulfide is bubbled through until no more black precipitate is formed. The black precipitate is removed by filtering through a pad of diatomaceous earth. The filtrate is copiously washed with water and dried over anhydrous magnesium sulfate. The solvent is removed in vacuo to give a red, solid residue. The residue is chromatographed on silica gel preparative thin layer chromatographic plates, eluting with 3% methanol in methylene chloride to yield 38.8 mg. of a regioisomeric mixture of (±)-6,7,8,9-tetrahydro-5,7,10-and 5,8,10-trihydroxy-7-and-8-acetylanthra[2,3-b]thiophene-4,11-dione-7-and-8-acetate as a red solid.

To a stirred solution of 56.0 mg. of the preceding compound (prepared as described above) in 600 ml. of carbon tetrachloride is added a solution of 36.0 mg. of bromine in 10 ml. of carbon tetrachloride and a 10-15 mg. amount of azoisobutyronitrie. The resulting mixture is heated to 100° C. under nitrogen and stirred at this temperature for 30 minutes. After cooling to room temperature, the mixture is concentrated to 100 ml., then a solution containing 1.0 g. of potassium carbonate, 50 ml. of tetrahydrofuran and 50 ml. of water is added with vigorous stirring for 15 minutes at ambient temperature. The mixture is quenched with 10% aqueous oxalic acid, then is extracted with chloroform. The chloroform extracts are combined, copiously washed with water and dried over anhydrous sodium sulfate. The solvent is evaporated in vacuo to provide a red solid residue. The residue is chromatographed on silica gel preparative thin layer chromatographic plates and eluted with 3% methanol in methylene chloride to give a regioisomeric mixture of (±)-6,7,8,9-tetrahydro-9-and-6-epi-5,7,9,10-and 5,6,8,10-tetrahydroxy-7-and-8-acetylanthra[2,3-b]thiophene-4,11-dione-7-and-8-acetate.

To a solution of 24.3 mg. of the above compound in 25 ml. of methanol is added 0.1 ml. of saturated aqueous potassium carbonate. The mixture is degassed and flushed with nitrogen three times. The purple mixture is stirred under nitrogen for three hours, then is quenched with 10% aqueous oxalic acid. The crude product mixture is extracted with chloroform. The combined chloroform extracts are dried over anhydrous sodium sulfate and evaporated to dryness. The resulting red solid is chromatographed on silica gel preparative thin layer chromatographic plates and eluted with 3% methanol in methylene chloride to yield 14.1 mg. of a regioisomeric mixture of cis-(±)-6,7,8,9-tetrahydro-5,7,9,10-and 5,6,8,10-tetrahydroxy-7-and-8-acetylanthra[2,3-b]thiophene-4,11-dione.

A 41.8 mg. amount of the preceding cis-material (prepared as described above) is dissolved in 5.0 ml. of chloroform (dried over aluminum oxide) and is treated with 70.9 mg. of mercuric cyanide, 46.4 mg. of mercuric bromide and 200 mg. of 3 A° molecuar sieves. This slurry is stirred under nitrogen for one hour, then 85.0 mg. of 4-O-p-nitrobenzoyl-3-N-trifluoroacetyl daunosaminyl chloride (prepared from di-p-nitrobenzoyl sugar) is added. The mixture is stirred overnight under nitrogen then is treated again with additional identical portions as above of mercuric cyanide, mercuric bromide, 3 A° molecular sieves and chlorosugar. Twenty-four hours after the second portion of sugar is added the mixture is filtered through a plug of glass wool. The filtrate is washed with two 50 ml. portions of 30% aqueous potassium iodide then with water. The organic solvent is dried over sodium sulfate and evaporated in vacuo. The residue is chromatographed on 0.5 mm. silica gel preparative thin layer chromatographic plates to yield 50.5 mg. of α-anomer 7β(and/or 8α)acetyl-9α(and/or 6β)-[2,3,6-trideoxy-4-O-(4-nitrobenzoyl-3-[(trifluoroacetyl)amino]-α-L-lyxo-hexopyranosyl]oxy-6,7,8,9-tetrahydro-5,7α,10(and/or 5,8β,10)-trihydroxyanthra[2,3-b]thiophene-4,11-dione and 26.5 mg. of β-anomer.

A 11.5 mg. portion of the α-anomer above is dissolved in 2.5 ml. of tetrahydrofuran and chilled to 0°-5° C. in a ice-water bath. The mixture is treated with 1.5 ml. of cold 0.1 N sodium hydroxide, degassed three times, then stirred under nitrogen for 4.5 hours at 0°-5° C. The mixture is acidified to pH 6.0 with 0.1 N hydrochloric acid. The tetrahydrofuran is removed in vacuo and the resulting aqueous solution is filtered and the aqueous filtrate is made basic to pH 9.0 with 0.1 N sodium hydroxide and is extracted with chloroform until the aqueous layer is colorless (after each extraction the mixture is readjusted to pH 9.0). The combined basic extracts are washed with saturated sodium bicarbonate, dried over sodium sulfate and evaporated in vacuo to yield the free base. The free base is diluted with one ml. of chloroform and treated with 0.01 ml. of 0.18 N ethanolic hydrogen chloride. The amine hydrochloride is precipitated with 7.0 ml. of anhydrous diethyl ether. The solvent is removed by decantation and the residue is air dried to yield 2.4 mg. of 7β(and/or 8α)-acetyl-9 (and/or 6β)-[(3-amino-2,3,6-trideoxy-α-L-lyxo-hexopyranosyl)oxy]-6,7,8,9-tetrahydro-5,7α,10-(and/or 5,8β,10)-trihydroxyanthra[2,3-b]thiophene-4,11-dione hydrochloride as a brownish red solid.

When the β-anomer product above is treated as described, 7β(and/or 8α)-acetyl-9α(and/or 6β)-[(3-amino-2,3,6-trideoxy-β-L-lyxo-hexopyranosyl)oxy]-6,7,8,9-tetrahydro-5,7α,10-(and/or 5,8β,10)-trihydroxyanthra[2,3-b]thiophene-4,11-dione, hydrochloride is obtained.

EXAMPLE 3

8α-Hydroxyacetyl-6β-[(3-amino-2,3,6-trideoxy-α-L-lyxo-hexopyranosyl)oxy]-6,7,8,9-tetrahydro-5,8β,10-trihydroxyanthra[2,3-c]thiophene-4,11-dione, hydrochloride A 21.7 mg. amount of 8α-acetyl-6,7,8,9-tetrahydro-5,6β,8β,10-tetrahydroxyanthra[2,3-c]thiophene-4,11-dione is dissolved in 2.0 ml. of chloroform and is treated with 0.36 ml. of 0.16 M. bromine in chloroform. The mixture is allowed to stand at room temperature for 36 hours. The precipitate is collected and washed with a minimum amount of chloroform to yield 17.3 mg. of 8α-bromoacetyl-6,7,8,9-tetrahydro-5,6β,8β,10-tetrahydroxyanthra[2,3-c]thiophene-4,11-dione.

A 12.3 mg. portion of the above product is suspended in 13 ml. of 80% aqueous acetone and heated to 55°-60° C., then 271 ml. of 0.1 N sodium hydroxide is added and the mixture is heated an additional 5 minutes with stirring under nitrogen. The reaction mixture is cooled, diluted with chloroform and poured into water. The organic layer is separated and the aqueous phase is extracted with chloroform until colorless. The chloroform solutions are combined, dried over sodium sulfate and evaporated in vacuo to give 9.1 mg. of 8α-hydroxyacetyl-6,7,8,9-tetrahydro-5,6β,8β,10-tetrahydroxyanthra[2,3-c]thiophene-4,11-dione.

A 24.0 mg. amount of the preceding compound (prepared as described above) is dissolved in 2.0 ml. of dry pyridine, then 190 mg. of anisylchlorodiphenylmethane is added at once at 0° C. with stirring. The reaction mixture is placed in a refrigerator and monitored by thin layer chromatography. After 4 days, the reaction mixture is poured into water and extracted with chloroform. The combined extracts are washed with 3 N sulfuric acid, aqueous sodium bicarbonate and water, then dried over anhydrous sodium sulfate and evaporated in vacuo. The residue is chromatographed on 0.5 mm. silica gel preparative thin layer chromatographic plates to yield 23.8 mg. of 8α-[(p-methoxy-α,α'-diphenylbenzyloxy)acetyl]-6,7,8,9-tetrahydro-5,6β,8β,10-tetrahydroxyanthra[2,3-c]thiophene-4,11-dione.

A 30.0 mg. amount of the above product (prepared as described), 69.0 mg. of mercuric bromide, 133 mg. of mercuric cyanide and 266 mg. of powdered 3A molecular sieve in 5.0 ml. of tetrahydrofuran is heated to 40°-45° C. for 1.5 hours with stirring. Then one molar equivalent portions of freshly prepared 4-0-p-nitrobenzoyl-3-N-trifluoroacetyldaunosaminyl chloride (chlorosugar) is added at 0, 3, 7, 19, 21 and 24 hours while the mixture is maintained at 40°-45° C. (The chlorosugar is prepared by suspending 24.5 mg. of 1,4-di-o-p-nitrobenzoyl-N-trifluoroacetyl daunosamine in one ml. of dry dichloromethane, then cooling the mixture to 0° C. in a ice bath and bubbling hydrogen chloride gas through the mixture for 3 minutes. The reaction mixture is allowed to stand at room temperature for 10 minutes, then p-nitrobenzoic acid is removed by filtration. The solvent is removed in vacuo and the residue is dried under reduced pressure and then dissolved in one ml. of dry dichloromethane). The mixture is stirred for 7 hours under nitrogen then is treated again with additional identical portions as above of mercuric cyanide, mercuric bromide, and powdered 3A molecular sieve. After a total reaction time of 29 hours after the first addition of chlorosugar the reaction mixture is filtered and the solid is washed with chloroform. The combined filtrates are washed with 30% aqueous potassium iodide, aqueous sodium bicarbonate and water, dried over sodium sulfate and evaporated in vacuo. The residue is chromatographed on 0.5 mm. silica gel preparative thin layer chromatographic plates to yield 61.3 mg. of 8α-[(p-methoxy-α,α'-diphenylbenzyloxy)acetyl]-6,7,8,9-tetrahydro-5,8β,10-trihydroxy-6β{[2,3,6-trideoxy-4-0-(4-nitrobenzoyl)-3-[(trifluoroacetyl)amino]-L-lyxo-hexopyranosyl]oxy}-anthra[2,3-c]thiophene-4,11-dione.

A 82.5 mg. amount of the preceding product (prepared as described above) is dissolved in 43 ml. of tetrahydrofuran and is cooled to 3° C. in an ice-water bath. A cold solution of 40 ml. of 0.01 M barium hydroxide is added dropwise and the resulting mixture is degassed three times. The mixture is stirred under nitrogen for one hour and 15 minutes then is neutralized to pH 8 with 0.1 N hydrochloric acid and is extracted with chloroform until no more colored material is taken into the chloroform. During the extractions the pH of the aqueous phase is maintained at pH 8. The combined chloroform extracts are washed with aqueous sodium bicarbonate and water, dried over anhydrous sodium sulfate and evaporated to give 8α[(p-methoxy-α,α'-diphenylbenzyloxy)acetyl]-6,7,8,9-tetrahydro-5,8β,10-trihydroxy-6β}[3-amino-2,3,6-trideoxy- -L-lyxo-hexopyranosyl]oxy}anthra[2,3-c]-thiophene-4,11-dione.

The above product is dissolved in 4.0 ml. of 80% aqueous acetic acid and is stirred for 16 hours at room temperature. The solvent is removed under reduced pressure below 0° C. and the residue is dissolved in 2.0 ml. of methanol-chloroform (2:1) and is filtered. The filtrate is treated with 0.5 ml. of 0.2 N ethanolic hydrogen chloride followed by 20 ml. of ether.

The precipitate is collected by centrifugation and decantation. The residue obtained is dried under reduced pressure to give 5.5 mg. of the product of the Example.

We claim:

1. A compound selected from the group consisting of those of the formula:

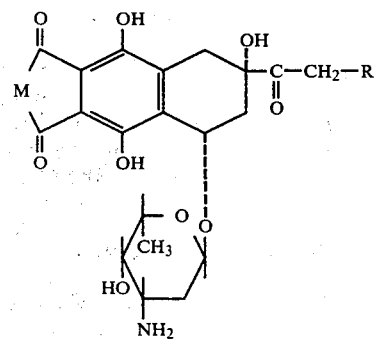

wherein R is hydrogen or hydroxy and M is a divalent moiety of the formulae:

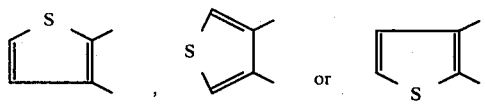

and the hydrochloride salts thereof.

2. The compound according to claim 1 wherein R is hydrogen, M is [2,3-c]thiophene, and the hydrochloride salt form; 8α-acetyl-6β-[(3-amino-2,3,6-trideoxy-α-L-lyxo-hexopyranosyl)oxy]-6,7,8,9-tetrahydro-5,8β,10-trihydroxyanthra[2,3-c]thiophene-4,11-dione, hydrochloride.

3. The compound according to claim 1 wherein R is hydrogen, M is [2,3-b]thiophene, and in the hydrochloride salt form; 8α-acetyl-6β-[(3-amino-2,3,6-trideoxy-α-L-lyxo-hexopyranosyl)oxy]-6,7,8,9-tetrahydro-5,8β,10-trihydroxyanthra[2,3-b]thiophene-4,11-dione, hydrochloride.

4. The compound according to claim 1 wherein R is hydroxy, M is [2,3-c]thiophene, and in the hydrochloride salt form; 8α-hydroxyacetyl-6β-[(3-amino-2,3,6-trideoxy-α-L-lyxo-hexopyranosyl)oxy]-6,7,8,9-tetrahydro-5,8β,10-trihydroxyanthra[2,3-c]thiophene-4,11-dione, hydrochloride.

5. The compound according to claim 1 wherein R is hydrogen, M is [2,3-b]thiophene, and in the hydrochloride salt form; 7β-acetyl-9α[(3-amino-2,3,6-trideoxy-α-L-lyxo-hexopyranosyl)oxy]-6,7,8,9-tetrahydro-5,8β,10-trihydroxyanthra[2,3-b]thiophene-4,11-dione, hydrochloride.

6. The compound according to claim 1 wherein R is hydrogen, M is [2,3-b]thiophene, and in the hydrochloride salt form; 8α-hydroxyacetyl-6β-[(3-amino-2,3,6-trideoxy-α-L-lyxo-hexopyranosyl)oxy]-6,7,8,9-tetrahydro-5,8β,10-trihydroxyanthra[2,3-b]thiophene-4,11-dione, hydrochloride.

7. The compound according to claim 1 wherein R is hydrogen, M is [,23-b]thiophene, and in the hydrochloride salt form; 7β-hydroxyacetyl-9α-[(3-amino-2,3,6-trideoxy-α-L-lyxo-hexopyranosyl)oxy]-6,7,8,9-tetrahydro-5,8β,10-trihydroxyanthra[2,3-b]thiophene-4,11-dione, hydrochloride.

8. A compound selected from the group consisting of those of the formula

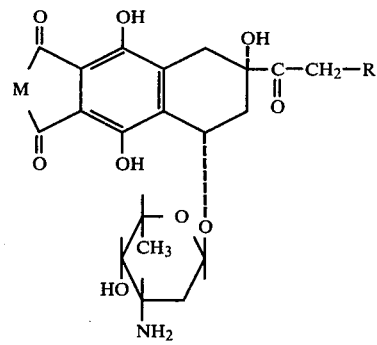

wherein R is hydrogen or hydroxy and M is a divalent moiety of the formulae:

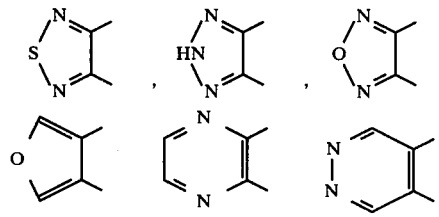

and the hydrochloride salts thereof.

* * * * *